United States Patent [19]

Tseng et al.

[11] Patent Number: 5,605,685
[45] Date of Patent: Feb. 25, 1997

[54] NON-IRRITATING SKIN AND HAIR REJUVENATING COMPOSTION HAVING A PH BETWEEN 1 AND 6.5

[75] Inventors: Susan Y. Tseng, Staten Island, N.Y.; Michael W. Helioff, Westfield, N.J.; Jui-Chang Chuang, Wayne, N.J.; H. Karl Krummel, Montville, N.J.; Mary R. Davis, Suffern, N.Y.

[73] Assignee: ISP Investments Inc., Wilmington, Del.

[21] Appl. No.: 565,605

[22] Filed: Nov. 30, 1995

Related U.S. Application Data

[63] Continuation-in-part of Ser. No. 528,383, Sep. 13, 1995.

[51] Int. Cl.$^6$ ............ A61K 7/00; A61K 31/19; A61K 47/32
[52] U.S. Cl. .................... 424/78.03; 424/78.32
[58] Field of Search ................ 424/78.02, 78.03, 424/78.04

[56] References Cited

U.S. PATENT DOCUMENTS

| | | | |
|---|---|---|---|
| 4,769,427 | 9/1988 | Nowakowsky et al. | 526/263 |
| 4,985,239 | 1/1991 | Yahagi et al. | 424/70.12 |
| 5,283,305 | 2/1994 | Chuang et al. | 526/263 |

FOREIGN PATENT DOCUMENTS

| | | | |
|---|---|---|---|
| 3006635 | 8/1981 | Germany | 424/78.03 |

*Primary Examiner*—Peter F. Kulkosky
*Attorney, Agent, or Firm*—Marilyn J. Maue; Walter Katz; Joshua J. Ward

[57] ABSTRACT

This invention relates to an acidic non-irritating lotion, cream or ointment for rejuvenating skin and hair which comprises a micronized, homogenized hydrogel of a crosslinked N-vinyl lactam polymer and an organic rejuvenating agent selected from the group consisting of pyruvic acid, a mono- or poly-carboxylated $C_1$ to $C_{20}$ hydrocarbon optionally substituted with from 1 to 3 hydroxy groups and ammonium and alkali metal salts of said acids and mixtures thereof including mixtures of the acids and/or said salts.

28 Claims, No Drawings

NON-IRRITATING SKIN AND HAIR REJUVENATING COMPOSTION HAVING A PH BETWEEN 1 AND 6.5

This application is a continuation-in-part of U.S. patent application, Ser. No. 528,383, filed Sep. 13, 1995, for HOMOGENIZED FLOWABLE HYDROGEL OF CROSSLINKED N-VINYL LACTAM POLYMER.

BACKGROUND OF THE INVENTION

1. Field of the Invention

This invention relates to a cosmetic lotion, cream or ointment, and, more particularly, to a cosmetic non-irritating, texture enhancing, homogenized composition for rejuvenating the appearance of skin or hair without irritation or damage which is a flowable, micronized composition having a pH of from 1 to 6.5, more desirably 3–4, and which comprises a micronized, homogenized, lightly crosslinked N-vinyl lactam polymer hydrogel and a rejuvenating agent selected from the group consisting of a carboxylated hydrocarbon optionally mono- or poly-substituted with a carbonyl or hydroxy group and an ammonium or alkali metal salt thereof or mixtures of said acids or acid and salts, or an aqueous, alcoholic or aqueous-alcoholic solution of said composition.

2. Description of the Prior Art

Cosmetic compositions having an alpha- or beta-hydroxy acid (AHA/BHA) as the active ingredient are well-known in the art. These compositions are useful in the treatment of the skin, particularly for anti-aging, skin smoothing, improvement in skin tone, reduction of fine lines, enhancement and control of desquamation in individuals with hyperkeratosis and the like. Application of such compositions generally results in a younger-looking skin as new cells replace the old. Smith, in Soap/Cosmetics/Chemical Specialties, Sept. 1993, page 54, addressed the question of whether an AHA must be in the acid form to be effective in promoting exfoliation and skin renewal. Various acids were examined for their ability to increase cell renewal at different pHs, with similar results observed for all acids tested. As the pH increased, the ability to stimulate cell renewal diminished; in fact, at a pH above 6, very little if any stimulation of the skin was observed with any AHA compounds. For the acids tested at selected pH levels, a maximal stimulation of renewal was observed at a pH of about 3, as shown in Table 1 below.

TABLE 1

Relationship between Cell Renewal, Irritation & pH for Various Acids Tested

| TEST MATERIAL | pH | CELL RENEWAL* | IRRITATION* |
|---|---|---|---|
| 4% Lactic acid | 3 | 35 | 2.8 |
| | 5 | 24 | 2.1 |
| | 7 | 13 | 1.2 |
| 4% Glycolic acid | 3 | 34 | 2.9 |
| | 5 | 23 | 2.1 |
| | 7 | 10 | 1.1 |
| 4% Salicylic acid | 3 | 42 | 3.0 |
| | 5 | 28 | 2.3 |
| | 7 | 12 | 1.2 |
| 5% Citric acid | 3 | 18 | 2.3 |
| | 5 | 14 | 2.1 |
| | 7 | 8 | 1.1 |

*A higher number indicates improved cell renewal/more irritation

Accordingly, to achieve improvement in skin condition, it has been necessary for the user to endure accompanying skin irritation caused by the presence of effective amounts of the acid. Accordingly, skin irritation is a major concern in the formulation of alpha and beta-hydroxy acid-containing products, particularly at acid loading levels which can deliver faster and more effective skin peeling which can be as high as, e.g. 45% to achieve chemical defoliation of the skin.

Goldenberg, R., in DCI/Jan. 1995, pages 37–44, entitled "Minimizing Irritation in Cosmetic Foundations", at page 42, stated that "PVP doesn't have the glamour botanical image of herbal extracts, but it has been reported to work effectively as an anti-irritant (at 1 percent) in a pH 3.0 polyvinyl alcohol mask containing 8 percent lactic acid as a moisturizer. A problem in all this is that hardly anyone has published AHA irritation studies".

Accordingly, it is an object of this invention to provide a cosmetic composition for the rejuvenation of skin or hair with substantially no irritation during use pH levels of 4 or below.

It is another object of this invention to provide a cosmetic composition for reducing hair dryness and rejuvenation of the hair appearance by reducing conditioner build-up.

Another object is to provide an improved thickener for liquid formulations.

Still another object is to provide a non-irritating, rejuvenating skin composition containing high concentrations of acid or a salt thereof.

These and other objects and features of the invention will become apparent from the following description and disclosure.

THE INVENTION

In accordance with this invention there is provided a non-irritating lotion, cream or ointment for rejuvenating skin or hair which comprises a flowable homogenized composition of a micronized, lightly crosslinked* N-vinyl lactam polymer and an organic rejuvenant selected from the group consisting of (1) pyruvic acid, (2) a mono- or poly-carboxylated $C_1$ to $C_{20}$ hydrocarbon optionally substituted with from 1 to 3 hydroxy groups, (3) an ammonium or alkali metal salt of said acids and any combination in mixtures of (1), (2) and/or (3).

*(CL)

The weight ratio of the hydrogel polymer to rejuvenant in the composition is between about 1:1 and about 999:1, i.e. 50–0.1 wt. % rejuvenant with respect to polymer. Preferably, for general consumer use, the weight % rejuvenant with respect to polymer is between about 1 and about 25 wt. %; although for professional skin defoliation preferred amounts of rejuvenant up to 40% or more are used.

General formulations for the composition of the present invention which can be directly applied to the skin or hair without irritation or damage and which may contain optional additives are illustrated in Table 2.

TABLE 2

|  | Composition of Invention (wt. %) | |
| --- | --- | --- |
|  | Suitable | Preferred |
| Essential Components | | |
| Rejuvenant | 0.1 to 50 | 1 to 25 |
| Micronized CL Polymer hydrogel (1–10% solids) | 50 to 99.9 | 75 to 99 |
| Optional Adjuvants based on total Composition of Essential Components | | |
| Water | 0 to 95 | |
| Emollient | 0 to 30 | 1–20 |
| Moisturizer | 0 to 30 | 1–20 |
| Neutralizer | 0 to 1.5 | 0.1–0.4 |
| Preservative | 0 to 1.0 | 0.1–0.5 |
| pH of above | 1.5 to 5.0 | 2–4 |

The micronized, homogenized hydrogel of this invention, which is derived from the homopolymerization or copolymerization of N-vinyl pyrrolidone and/or N-vinyl caprolactam and which is between about 0.01 and about 5% crosslinked, preferably between about 0.1 and about 2% crosslinked, with a suitable polyfunctional crosslinking agent, can be prepared by the process described in copending patent application Ser. No. 528,383, incorporated herein by reference. These crosslinked hydrogels are of a flowable consistency containing 1 to 15 wt. % solids, preferably 2–6 wt. % solids, and have a particle size which passes through a 40 to 350 mesh screen.

As indicated, the N-vinyl lactam monomer may be combined with a polymerizable comonomer, preferably in an amount not more than 30% comonomer. Suitable comonomers include olefinically unsaturated compounds such as another N-vinyl pyrrolidone, N-vinyl caprolactam, N-vinyl formamide, vinyl acetate, α-olefin, styrene, ammonium and alkali metal salts of acrylic acid and methacrylic acid, acrylamide, methacrylamide, lower alkyl acrylates or methacrylates, acrylonitrile, vinyl chloride, hydroxyalkyl acrylates or methacrylates, hydroxybutyl vinyl ether, quaternized dimethylamino lower alkyl acrylates or methacrylates or acrylamide or methacrylamides and the like.

Representative of the crosslinking agents which can be employed are diallylimidazolidone; divinyl ether of diethylene glycol; pentaerythritol triallyl ether (PETE); triallyl-1,3,5-triazine-2,4,6-(1H,3H,5H)trione (TATT); ethylene glycol diacrylate; 2,4,6-triallyloxy-1,3,5-triazine; N-vinyl-3(E)-ethylidene pyrrolidone (EVP); 1,7-octadiene; 1,9-decadiene; divinyl benzene; methylenebis(methacrylamide); methylenebis(acrylamide); N,N-divinylimidazolidone; ethylene glycol diacrylate; ethylidene his(N-vinyl pyrrolidone) (EBVP); etc.

Preferred hydrogel products of this invention are those derived from N-vinyl pyrrolidone homopolymer or N-vinyl pyrrolidone/N-vinyl caprolactam copolymer which are crosslinked with EVP, EBVP or divinylimidazolidone. Most preferred is the EVP crosslinked N-vinyl pyrrolidone homopolymer.

Most desirably, the flowable, homogenized hydrogel microparticles of the present invention pass through a 70–150 mesh screen and the micronized gel has a Brookfield viscosity (RV Model, #7 spindle, 20 rpm) of from about 5,000 to about 70,000 cps for about 2–6% solids; although hydrogel viscosities as low as 3,000 cps up to about 90,000 are also considered within the scope of this invention.

As indicated above, the rejuvenant can be an aromatic or saturated aliphatic carboxylated, optionally hydroxylated compound or mixture thereof. The aliphatic hydroxy acid of 4 or more carbon atoms are those having at least one hydroxy group in the alpha or beta position in the acid molecule, i.e. AHA or BHA compounds. Examples of such hydroxy acids include citric, gallic, glycolic, α-hydroxycaprylic, α-hydroxydecanoic, α-hydroxylauric, α-hydroxyoctanoic, α-hydroxypalmitic, α-hydroxysebacic, α-hydroxystearic, lactic, malic, salicylic and tartaric acids and mixtures thereof and multifruit acid mixtures. It is to be understood that said acids can be formed in situ upon addition to the hydrogel. Such hydrolyzable compounds include esters, peracids, and the like. Of the active rejuvenants in the present compositions, the hydroxylated, carboxylated acids of from 3 to 7 carbon atoms and said salts of these acids are preferred, lactic acid and its salts being most preferred.

The present composition can be prepared by adding the rejuvenant to the non-homogenized or to the homogenized N-vinyl lactam hydrogel in the process described in parent application, Ser. No. 528,383. In the former case, the rejuvenant is added during the water digestion stage and the mixture of polymer and rejuvenant are homogenized and micronized together to provide an intimately mixed, uniformly distributed acid active product. This method may result in some complexing between the acid and vinyl lactam components. In the later case, where the rejuvenant is gradually added to the micronized hydrogel and mixed until a uniform composition is obtained, an equally effective, non-irritating, anti-erythemal, rejuvenating composition is produced.

The concentrate compositions of the invention, containing from about 50 to about 99.9 wt. % hydrogel and 0.1 to 50% rejuvenant, can be applied directly to the skin or hair to achieve the desired effect such as sun blocking, desquamation, moisturizing, skin smoothing, clarification, depigmentation, softening, defoliantation, hair conditioning, bleaching, conditioner defilming, and other effects described in copending application Ser. No. 528,383.

Alternatively, when milder activity is desired, the concentrate composition can be mixed with a diluent; for example, mixed with 10 to about 50 volumes of water, alcohol or alcohol/water solution, based on total composition. Both the concentrate and the diluted product may include one or more of the optional additives mentioned above.

A neutralizer can be employed to adjust the pH of the composition, e.g. to raise the pH of the acid composition or solution from 1 to about 4 when rapid and strong action is not needed. Such neutralizers include sodium hydroxide, potassium hydroxide, ammonium hydroxide, monoethanolamine, diethanolamine and triethanolamine, and aminomethyl propanol.

Another optional component often included in the formulation is a preservative or mixtures thereof. The preservative concentration in the composition, based on the total weight of the composition, is in the range of between about 0.05% and about 1.5 wt. %, preferably between about 0.1% and about 0.5% wt. %. Suitable preservatives for use herein include sodium benzoate and propyl paraben, Germaben® II (Sutton Laboratories), Na hydroxymethyl glycinate (SUTTOCIDE® A) and mixtures thereof. Other conventional additives such as, for example, fragrances, coloring agents, sun-screens, etc. may also be included in the concentrate composition or a solution thereof. Ultraviolet absorbing agents, often described as sunscreening agents, can be present in a concentration in the range of between about 1% and about 12% by weight, based on the total weight of composition. Preferably, the UV absorbing agents, when employed, constitute between about 2% and 8% by weight, more often between about 4% and about 6% by weight, of the total composition. Of the ultraviolet absorbing agents suitable for use herein, benzophenone-3, benzophenone-4, octyl dimethyl PABA (Padimate O), octyl methoxy cinnamate, octyl salicylate, octocrylene, p-methylbenzylidene camphor, butyl methoxy dibenzoyl methane (Parsol 1789) and mixtures thereof.

Having generally described the invention, reference is now had to the following examples which illustrate preferred embodiments and comparisons concerning the preparation and use of the present products, however these examples are not to be construed as limiting to the scope of the invention which is more broadly described above and defined in the appended claims.

EXAMPLE 1

A homogeneous solution of 10.84 grams of N-vinyl pyrrolidone (VP), 0.0479 gram N-vinyl-3(E)-ethylidene pyrrolidone (EVP), 42.24 grams of distilled water and 0.1192 gram of tert-butylperoxy pivalate (LUPERSOL 11) was reacted under 25 mm Hg of nitrogen at 60° C. for 1.5 hours and then at 120° C. to 140° C. for 1.5 hours, after which the solution was allowed to cool to room temperature and the resulting rubbery product was then recovered and was introduced into about 800 ml of distilled water and digested for 15 hours with simultaneous removal and replacement of the water until the mother liquor is free of residual monomer and soluble poly-(N-vinylpyrrolidone). During the above water digestion step, the rubbery product swelled to a clear, transparent hydrogel mass having a gel volume of 18 grams water per gram of crosslinked polymer. This hydrogel product, was then introduced into a Ross homogenizer where, at 7,000 rpm the hydrogel mass is reduced to flowable hydrogel having a Brookfield viscosity of 30,000 cps which hydrogel is composed of colorless, clear particles which pass through a 40 mesh screen.

EXAMPLE 2

Hydrogel products obtained from crosslinking the compositions shown in Table 3 for 1 hour at 70° C. followed by 2 hours at 100° C. and digested in 10 fold volumes of water over a period of 16 hours to remove contaminants, were recovered as a hydrogel mass having the indicated wt. % solids. These samples were separately homogenized in a Ross Homogenizer at room temperature operated 7,000 rpm for 30 minutes, after which the products, having the properties reported in Table 4, were recovered.

TABLE 4

| Sample | A | B | C | D | E | F | G |
|---|---|---|---|---|---|---|---|
| Particle Size thru Screen (Mesh) | 40 | 70 | 70 | 70 | 70 | 70 | 70 |
| % Solids in homogenized microhydrogel | 5.4 | 3 | 5 | 2.8 | 3 | 1.84 | 6.1 |
| Brookfield Viscosity (cps) | 34,000 | | | 5,000 to 25,000 | | | 57.000 |

EXAMPLE 3

Separately prepared samples of Example 1 are admixed for 30 minutes with 10 wt. % of each of the following rejuvenants.
1. glycolic acid
2. salicylic acid
3. ammonium lactate
4. a 2:1:1 mixture of lactic, octanoic and decanoic acids.

The resulting creamy compositions of homogeneous, micronized hydrogel/rejuvenant concentrates are applied twice a day for 2 weeks as a film over areas of dry, flakey skin having several brownish sun spots. After 2 weeks, skin dryness is eliminated in the treated areas and skin spots are significantly faded to invisibility.

The same results are obtained when the above rejuvenants are added to the water digestion step in Example 1 and then subjected to homogenization with the hydrogel polymer.

The above homogenized, micronized hydrogel/rejuvenant compositions also can be mixed with an effective amount of a sun blocking agent or applied directly to the skin in a thin layer, to provide a water insoluble moisturizing during exposure to the sun. Further, the present products can be employed in 0.5–5 wt. % concentration in standard hair bleaches, hair dyes and hair straightening formulations to minimize scalp irritation or dryness while imparting a silky, soft feel to the hair which qualities are enhanced by the hydrogel microparticle superpenetrating properties of the compositions.

The following examples describe the preparation of several cosmetic and pharmaceutical compositions.

EXAMPLE 4

To an 8 ounce jar, containing 54.75 g of the flowable crosslinked PVP homogenized, micronized hydrogel of Sample 2A, 18.3 g of lactic acid (30% in distilled water) is gradually introduced with gentle mixing at ambient temperature for 10 minutes. The resulting product containing

TABLE 3

| | WEIGHT (GRAMS) | | | | | | |
|---|---|---|---|---|---|---|---|
| Sample | A | B | C | D | E | F | G |
| VP | 39.84 | 39.93 | 49.8 | 39.92 | 11.95 | 9.543 | 319.04 |
| EVP | 0.16 | 0.08 | 0.2 | 0.08 | 0.05 | 0.0454 | 0.96 |
| Lupersol | | | | | | | |
| 554* | 0.398 | 0.4 | 0.73 | 0.336 | 0.12 | — | 3.35 |
| 11** | — | — | — | — | — | 0.51 | |
| H₂O | 160 | 160 | 200 | 160 | 48 | 90 | 1280 |
| Solids in digested Hydrogel | 5.9 | 3 | 5 | 2.8 | 3 | 1.84 | 6.11 |

*tert-amylperoxy pivalate
**tert-butylperoxy pivalate

10% lactic acid is applied to the skin as a mild cleanser-defoliant without skin irritation.

EXAMPLE 5

Example 4 was repeated except that 0.30 g of lactic acid (88% aqueous solution) was substituted. The pH of the product, containing 0.5 wt. % lactic acid, was 3. The product was stable when inspected after 6 weeks storage. This product is spread on the skin as a cream to effect decoloration of brownish spots.

EXAMPLE 6

Example 5 was repeated except that 81.25 g of the homogenized, flowable hydrogel and 4.92 g of lactic acid were substituted. The product contained 5 wt. % lactic acid and had a pH of 2. The product was found to be stable when inspected after 6 weeks. This product is useful as a skin bleach and defoliant.

The following illustrate non-irritating facial conditioning formulations. All ingredients are mixed at room temperature in the order set forth below.

EXAMPLE 7

The following compositions were prepared by mixing the components at room temperature and the Brookfield viscosity (Model RV #7 spindle, 20 rpm) and gel stability of the compositions reported as shown below.

| Composition | |
|---|---|
| A: | 40 g. homogenized 2% crosslinked (CL) PVP hydrogel microparticles (3.36% solids). |
| B: | 10 g. aqueous lactic acid solution (85%) + A to provide a total 21.25 g. of mixture. |
| C: | 40.60 g. aqueous PVP K-30 (16.55% solids) + 159.4 g. STABILEZE ® gel (0.4% solids). |
| D: | 5.88 g. aqueous lactic acid solution (85%) + 44.12 g. of C. |
| E: | 0.47 g. lactic acid aqueous solution (85%) + 39.53 g. of C. |
| F: | 30 g. of 50/50 mixture A and STABILEZE ® gel (0.4% solids). |
| G: | 0.36 g. lactic acid aqueous solution (85%) + 30 g. of F. |

| Composition | Stability/Brookfield Viscosity RESULTS |
|---|---|
| A | Clear, stable/18,800 cps |
| B | clear, stable/20,000 cps |
| C | stable/30,000 cps |
| D | immediate pptn.- gel collapsed |
| E | immediate pptn.- gel collapsed |
| F | stable gel similar to C |
| G | ppt formed- composition was an opaque paste |

It was found that the stability of those compositions employing an added thickener such as STABILEZE to provide a gel consistency extended over a pH range of 4–9. At pH levels slightly below 4, the STABILEZE thickened gel is not stable to acid addition and at pH 2–3, such acid containing gels completely collapse. Conversely, the homogenized, micronized hydrogel is stable over the entire pH range of 1–12. A further advantage of the homogenized, micronized hydrogel compositions is the ability to load 40% or more of the active rejuvenant, e.g. lactic acid, without reduction in stability of the composition.

EXAMPLE 8

Comparison of Homogenized and Non-Homogenized PVP Hydrogels

The following hydrogel Samples (Y and Z) were prepared. Sample Y was a lightly EVP crosslinked, homogenized hydrogel (3.09% solids) prepared according to Example 2B of copending U.S. application Ser. No. 528,383. The hydrogel of Sample Z was a lightly PETE crosslinked powder, synthesized from heptane, which gel was prepared by addition of deionized water to the powder in an amount needed to provide a 3.17% solids emulsion.

Sample Y displays a remarkable distinction in gel clarity and viscosity over Sample Z as shown below.

| | Sample Y | Sample Z |
|---|---|---|
| Brookfield viscosity (RV #7, 20 rpm at 25° C.) | 5,400 cps | 1,800 cps |
| Clarity (HACH value) | 26.4 | 1,627 |

The following Examples 9 and 10 illustrate skin rejuvenating formulations.

EXAMPLE 9

| Components | wt. % |
|---|---|
| (a) Homogenized, micronized CL-PVP hydrogel (3.5% solids) of 70 mesh particle size | 60 |
| (b) Glycolic acid (70%; solids (Aldrich) | 23.5 |
| (c) Suttocide ® A | 0.5 |
| (d) 25% Aq. NaOH to adjust pH to 4 | q.s. |
| (e) Germaben II (Sutton) | 1.5 |
| (f) Disodium ethylenediamine tetraacetic acid | 0.1 |

EXAMPLE 10

| Components | wt. % |
|---|---|
| (a) Homogenized, micronized CL-PVP hydrogel (4% solids) of 70 mesh particle size | 60 |
| (b) α-hydroxyoctanoic acid | 18 |
| (c) Suttocide ® A | 0.5 |
| (d) 10% soln. NaOH to adjust pH to 3.5 | q.s. |
| (e) Germaben II | 1.5 |
| (f) deionized $H_2O$ | q.s. |

EXAMPLE 11

| FACIAL EXFOLIATING CREAM | |
|---|---|
| Components | wt. % |
| (a) Homogenized, micronized CL-PVP hydrogel (4% solids) of 60 mesh particle size | 68 |
| (b) tartaric acid | 30 |
| (c) Suttocide ® A | 0.5 |
| (d) Fragrance | 1.0 |
| (e) Colorant | 0.5 |

Noticeable exfoliation is achieved within 6 hours and a rosy, smooth skin texture results.

EXAMPLE 12

Anti-Irritation Testing

A comparative irritation test was conducted to determine the extent of reduction of irritation during use of a PVP-lactic acid composition. The results indicated that the addition of 3% PVP to 10% unneutralized lactic acid produced a significant reduction in irritation.

When applied to the face, a solution of unneutralized 10% lactic acid alone caused irritation of varying degrees in certain sensitive subjects. These sensitive individuals are used to compare the irritation caused by a 10% lactic acid solution to that caused by other test materials; in this case, a 10% lactic acid solution which contained 3% PVP.

In this study, a panel of 12 volunteers was selected from individuals who previously reported moderate stinging following application of the standard lactic acid solution, reported their reactions to a control solution of lactic acid and the test solution of 10% lactic acid with 3% PVP. Test materials were randomly applied with a cotton-tipped applicator to either the left or right naso-labial fold. Subjective reactions (on a scale of 0–3, with 0 being no irritation) were reported 10 seconds, 2.5 minutes, and 5 minutes after application. Results are as follows:

| Number of persons responding | Time after Application | | |
| --- | --- | --- | --- |
| | 10 sec | 2.5 min | 5 min |
| Lactic acid | 7/12 | 9/12 | 8/12 |
| Lactic acid and PVP K-30 | 3/12 | 4/12 | 2/12 |
| Irritation (sum of 1 + 2 + 3 reaction severity) | | | |
| Lactic acid | 8 | 13 | 9 |
| Lactic acid and PVP K-30 | 4 | 6 | 2 |

EXAMPLE 13

When Example 12 is repeated with substitution of 2% crosslinked polyvinylpyrrolidone/vinyl acetate (75/25) homogenized hydrogel for PVP, irritation is reduced to zero.

EXAMPLE 14

When Example 12 is repeated with the substitution of 2% crosslinked poly(vinylpyrrolidone/vinyl caprolactam) homogenized hydrogel for PVP, irritation is reduced to zero.

EXAMPLE 15

Cell Renewal Studies

A. This study evaluated the disappearance of dansyl chloride (5-dimethylaminonaphalene-1-sulfonyl chloride) from the stratum corneum of treated and control sites. Such disappearance is accepted as a marker of the transit of cells through the horny layer, and thus a function of the rate of new cell production.

The composition comprised about 150 ml of cream. 26 female panelists were patched for 24 hours with 5% dansyl chloride in a petroleum base. All subjects were examined on day 1 with a quartz mineral UV lamps (long and short wave) to ensure that the fluorescent stain had been taken up by the stratum corneum layers. Multifruit and 10% aqueous solution was applied to sites on the vulnar forearm over the dansyl chloride sites. The 10% dilution Multifruit BSC produced at least a 30% increase in cell renewal when compared to the untreated control site. Accordingly there was a 143% increase in the number of squames generated.

Evaluated at 4% in a commercial cream, Multifruit BSC increased cell turnover by 20% relative to the control formulation. However, cell renewal was accompanied by burning and skin reddening.

B. When the Multifruit acid or salicylic acid is mixed with homogenized 3% CL-PVP hydrogel (weight ratio 1:1.5) skin irritation and reddening are eliminated but cell renewal remains substantially the same.

EXAMPLE 16

When Example 15 is repeated, except for the substitution of lactic acid for Multifruit acid, the results are substantially the same.

Similar cell renewal with no skin irritation are obtained with the homogenized 3% CL-PVP hydrogel and 6% glycolic, tartaric, malic, octanoic and decanoic, lactic acid mixtures. Citric acid exhibited less cell renewal than the other hydroxy acids, although substantial cell renewal was obtained.

It will be understood that the above examples illustrate certain embodiments of the invention but that many modifications and variations in the homogenized hydrogel polymer/rejuvenant as described herein are within the scope of this invention.

What is claimed is:

1. A non-irritating, skin and hair rejuvenating composition having a pH of from about 1 and about 6.5 which comprises a flowable, homogenized composition of
    (a) a micronized, lightly crosslinked N-vinyl lactam hydrogel of 1–15 wt. % solids and
    (b) an active organic rejuvenating agent selected from the group consisting of
        (1) pyruvic acid,
        (2) mono- and poly-carboxylated $C_1$ to $C_{20}$ hydrocarbon optionally substituted with from 1 to 3 hydroxy groups,
        (3) an ammonium or alkali metal salt of (2) and mixtures of (1), (2) and/or (3).

2. The composition of claim 1 wherein the weight ratio of hydrogel to (b) is between about 1:1 and about 999:1.

3. The composition of claim 1 containing 50–99.9 wt. % (a) and 0.1–50 wt. % (b).

4. The composition of claim 3 containing 75–99 wt. % (a) and 1–25 wt. % (b).

5. The composition of claim 1 wherein said component (a) is 0.01–5% crosslinked micronized N-vinyl lactam hydrogel polymer.

6. The composition of claim 5 wherein said micronized hydrogel is a polymer derived from at least 70% N-vinyl lactam monomer.

7. The composition of claim 5 wherein (a) is N-vinylpyrrolidone hydrogel homopolymer.

8. The composition of claim 5 wherein (a) is N-vinyl caprolactam hydrogel homopolymer.

9. The composition of claim 5 wherein (a) is N-vinylpyrrolidone/N-vinyl caprolactam hydrogel copolymer.

10. The composition of claim 5 wherein (a) is a copolymer hydrogel of N-vinyl lactam and not more than 30% of an olefinically unsaturated comonomer.

11. The composition of claim 10 wherein (a) is a copolymer hydrogel of N-vinylpyrrolidone and vinyl acetate.

12. The composition of claim 1 wherein said rejuvenating agent contains a hydroxylated hydrocarbon having at least one carboxyl group and mixtures thereof.

13. The composition of claim 1 wherein said rejuvenating agent contains a $C_1$ to $C_{20}$ carboxylic acid or mixtures thereof.

14. The composition of claim 1 wherein said rejuvenating agent contains an ammonium or alkali metal salt of the mono- or poly-carboxylic acid optionally substituted with from 1 to 3 hydroxyl groups.

15. The composition of claim 1 wherein said rejuvenating agent is a mixture of (1) and (2).

16. The composition of claim 15 wherein said rejuvenating agent is a mixture of lactic, octanoic and decanoic acids.

17. The composition of claim 1 wherein said rejuvenating agent is lactic acid.

18. The composition of claim 1 wherein said rejuvenating agent is salicylic acid.

19. The composition of claim 1 wherein said rejuvenating agent is tartaric acid.

20. The composition of claim 1 wherein said rejuvenating agent is glycolic acid.

21. The composition of claim 1 which optionally contains up to about 1 wt. % preservative based on total composition.

22. The composition of claim 1 having a pH of 2 to 4.

23. The composition of claim 1 diluted with up to 95% water, alcohol or a mixture, based on total composition.

24. The composition of claim 1 wherein said micronized hydrogel has a particle size of from about 40 mesh to about 350 mesh.

25. The composition of claim 1 wherein said micronized hydrogel is derived from a 0.01 to 5% crosslinked N-vinyl lactam polymer hydrogel mass which is digested in water and then subjected to high shear agitation to produce microparticles of the hydrogel which pass a 40–350 mesh screen.

26. The process of applying to the skin or hair an effective rejuvenating amount of the composition of claim 1.

27. The process of claim 26 wherein said composition is applied to the skin and the effective amount is a skin defoliating amount.

28. The process of claim 26 wherein said composition is applied to the skin and the effective amount is a moisturizing amount.

* * * * *